(12) United States Patent
Spence et al.

(10) Patent No.: US 10,463,508 B2
(45) Date of Patent: *Nov. 5, 2019

(54) GRAFT ANCHOR DEVICES, SYSTEMS AND METHODS

(71) Applicant: Abiomed, Inc., Danvers, MA (US)

(72) Inventors: Paul Spence, Louisville, KY (US); Rob Dowling, Lousville, KY (US); Robert T. V. Kung, Andover, MA (US); Caitlyn Hastie, Billerica, MA (US); Thorsten Siess, Wuerselen (DE); Eric Gratz, Louisville, KY (US); Gerd Spanier, Aachen (DE)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/023,927

(22) Filed: Jun. 29, 2018

(65) Prior Publication Data

US 2018/0368997 A1 Dec. 27, 2018

Related U.S. Application Data

(63) Continuation of application No. 14/420,590, filed as application No. PCT/US2013/054398 on Aug. 9, 2013, now Pat. No. 10,143,571.

(60) Provisional application No. 61/681,988, filed on Aug. 10, 2012.

(51) Int. Cl.
| | |
|---|---|
| *A61F 2/856* | (2013.01) |
| *A61B 17/11* | (2006.01) |
| *A61M 1/10* | (2006.01) |
| *A61F 2/06* | (2013.01) |
| *A61M 1/12* | (2006.01) |

(52) U.S. Cl.
CPC .............. *A61F 2/856* (2013.01); *A61B 17/11* (2013.01); *A61M 1/1008* (2014.02); *A61B 2017/1107* (2013.01); *A61B 2017/1135* (2013.01); *A61F 2002/068* (2013.01); *A61M 1/12* (2013.01); *A61M 1/125* (2014.02)

(58) Field of Classification Search
CPC ...... A61F 2/04; A61F 2/28; A61F 2/06; A61F 2002/068; A61F 2002/0081; A61F 2/856; A61F 2/852
See application file for complete search history.

(56) References Cited

U.S. PATENT DOCUMENTS

| | | | |
|---|---|---|---|
| 3,667,069 | A | 6/1972 | Blackshear et al. |
| 3,871,471 | A | 3/1975 | Wong |
| 4,240,409 | A | 12/1980 | Robinson et al. |
| 4,573,576 | A | 3/1986 | Krol |

(Continued)

FOREIGN PATENT DOCUMENTS

| | | |
|---|---|---|
| EP | 2319456 A1 | 5/2011 |
| JP | 2002-501404 A | 1/2002 |

(Continued)

OTHER PUBLICATIONS

PCT International Search Report for International Application No. PCT/US2013/054398, dated Nov. 22, 2013 (2 pages).

(Continued)

*Primary Examiner* — Jason-Dennis N Stewart
(74) *Attorney, Agent, or Firm* — White & Case LLP

(57) ABSTRACT

The present disclosure provides medical devices, systems and methods and in particular to devices and methods useful for anchoring graft materials to bodily structures.

9 Claims, 13 Drawing Sheets

(56) References Cited

U.S. PATENT DOCUMENTS

| | | | |
|---|---|---|---|
| 5,084,064 A | 1/1992 | Barak et al. | |
| 5,327,885 A | 7/1994 | Griffith | |
| 5,849,036 A | 12/1998 | Zarate | |
| 6,015,431 A | 1/2000 | Thornton et al. | |
| 6,050,975 A | 4/2000 | Poirier | |
| 6,221,101 B1 | 4/2001 | Harris et al. | |
| 6,390,969 B1 | 5/2002 | Bolling et al. | |
| 6,488,692 B1 | 12/2002 | Spence et al. | |
| 6,524,322 B1 | 2/2003 | Berreklouw | |
| 7,108,673 B1 | 9/2006 | Batiste | |
| 9,381,286 B2 | 7/2016 | Spence et al. | |
| 2002/0058984 A1 | 5/2002 | Butaric et al. | |
| 2002/0095210 A1 | 7/2002 | Finnegan et al. | |
| 2002/0179166 A1 | 12/2002 | Houston et al. | |
| 2003/0225448 A1 | 12/2003 | Gerberding | |
| 2005/0096496 A1 | 5/2005 | Spence | |
| 2005/0119573 A1 | 6/2005 | Vilenkin et al. | |
| 2005/0267559 A1 | 12/2005 | De Oliveira | |
| 2006/0020242 A1 | 1/2006 | Yamazaki et al. | |
| 2006/0074271 A1 | 4/2006 | Cotter | |
| 2007/0208290 A1 | 9/2007 | Pecor et al. | |
| 2008/0140110 A1 | 6/2008 | Spence | |
| 2008/0167595 A1 | 7/2008 | Porter et al. | |
| 2009/0048663 A1 | 2/2009 | Greenberg | |
| 2009/0076531 A1 | 3/2009 | Richardson et al. | |
| 2010/0010413 A1 | 1/2010 | Loiterman et al. | |
| 2010/0280306 A1 | 11/2010 | Spence | |
| 2010/0312333 A1 | 12/2010 | Navia et al. | |
| 2010/0324667 A1 | 12/2010 | King | |
| 2011/0060398 A1 | 3/2011 | Tupil et al. | |
| 2012/0130314 A1 | 5/2012 | Stonebridge et al. | |
| 2014/0316189 A1 | 10/2014 | Spence et al. | |
| 2015/0216685 A1 | 8/2015 | Spence et al. | |
| 2015/0265757 A1 | 9/2015 | Dowling et al. | |
| 2016/0354524 A1 | 12/2016 | Dowling et al. | |

FOREIGN PATENT DOCUMENTS

| | | |
|---|---|---|
| JP | 2007-195995 A | 8/2007 |
| JP | 2010-505515 A | 2/2010 |
| WO | 199852495 | 11/1998 |
| WO | 199962415 | 12/1999 |
| WO | 0038591 A2 | 7/2000 |
| WO | 2005077305 A1 | 8/2005 |
| WO | 2007061787 A2 | 5/2007 |
| WO | 2010133848 A1 | 11/2010 |
| WO | 2011/081814 A1 | 7/2011 |
| WO | 2012125927 A2 | 9/2012 |
| WO | 2013023009 A1 | 2/2013 |

OTHER PUBLICATIONS

PCT International Search Report for International Application No. PCT/US12/66292, dated Feb. 5, 2013 (3 pages).

PCT International Search Report for International Application No. PCT/US12/50604, dated Oct. 23, 2012 (3 pages).

Supplementary European Search Report—EP 12 83 3552 dated Feb. 25, 2015 (2 pages).

GRAFT ANCHOR DEVICES, SYSTEMS AND METHODS

CROSS REFERENCE TO RELATED APPLICATIONS

This application is a continuation of U.S. application Ser. No. 14/420,590, filed Feb. 9, 2015, which is a national stage filing under 35 U.S.C. § 371 of International Application No. PCT/US13/54398, filed on Aug. 9, 2013, which claims priority to U.S. Provisional Application Ser. No. 61/681,988, filed Aug. 10, 2012. The specifications of each of the foregoing applications are hereby incorporated by reference in their entirety.

TECHNICAL FIELD

The present disclosure relates generally to medical devices and in particular to devices and methods useful for anchoring graft materials to bodily structures.

BACKGROUND

Implant materials that facilitate tissue ingrowth, such as grafts, may be used in the medical arts, particularly in applications involving vascular replacement, augmentation, and/or repair. These materials may be naturally-derived or non-naturally-derived, and when they are implanted within a patient, cells and other bodily substances from the patient can infiltrate the material, leading to, for example, new tissue growth on, around, and/or within the implanted material. Tissue ingrowth may enhance the biocompatibility of such implants, but excessive tissue growth may result in unwanted complications.

Such grafts and graft anchoring devices may be used in implantable Ventricular Assist Devices (VAD) to create inflow and outflow conduits that interface with the circulatory system. Control of cellular ingrowth has been one of the main challenges for such devices when implanted for long periods of time.

SUMMARY

The present disclosure provides, in certain aspects, unique methods and systems for anchoring graft materials to the walls of bodily structures. Some methods and systems involve anchoring a first graft component to a wall of a bodily structure, wherein new tissue growth on, around, and/or within the first graft is facilitated. The first graft component is intended to provide a cuff structure to allow the anchoring of a second graft component easily. The second graft and first graft component may have the same or substantially similar material, biological characteristics, mechanical characteristics, and/or dimensions. Alternatively, the second graft component may have distinct material, biological characteristics, mechanical characteristics, and/or dimensions from the first graft component. The graft could be formed of two or more similar or different components.

In another embodiment, the disclosure provides a graft formed by components that have different characteristics that could be joined together to give different characteristics to different parts of the graft.

In another embodiment, the disclosure provides techniques to limit cellular ingrowth to the proximal component of the graft but not to other components; therefore cellular propagation is limited to one or more components but not to all components.

In another embodiment, the disclosure provides techniques used to have different diameter grafts joined in such a way that a vortex could be formed in sections of the graft to enhance "washout" effect in certain sections of the graft and therefore limit any cellular growth or attachment in such sections of the graft.

In another embodiment, the disclosure provides techniques used to have a single graft that is equipped by internal deformity to intentionally create a vortex in the flow in order to disrupt any cellular buildup in such area.

In another embodiment, the disclosure provides techniques used to have a single graft having different internal structure or characteristics in different regions to enhance certain reaction or behavior in certain regions while other sections inhibit certain reactions and behaviors.

In one embodiment a vascular graft is provided. The vascular graft includes at least one conduit having a first conduit region and a second conduit region. The vascular graft further includes at least one perturbation formed in the conduit in the second conduit region, the perturbation configured to cause a vortex in the second conduit region.

The first conduit region may include a first material and the second conduit region may include a second material distinct from the first material. The first material may include silicone rubber. The second material may include porous ePTFE. The second material may include woven Dacron®.

The at least one perturbation may decrease the inner diameter of the conduit region. The at least one perturbation may be tapered.

The first conduit region and the second conduit region may have substantially the same diameter.

The vascular graft may include a blood flow assist system coupled to the at least one conduit.

Another embodiment provides a vascular graft that includes at least one conduit having a first conduit region and a second conduit region. The second conduit region includes a bulbous portion with respect to the first conduit region. The graft further includes at least one first support strut positioned in the first conduit region. The at least one first support strut is formed in a spiral configuration. The graft further includes at least one second support strut position in the second conduit region.

The at least one second support strut may be sutured to an outer wall of the bulbous portion of the second conduit region.

The at least one second support strut may be composed of stainless steel wires.

The system may include a blood flow assist system coupled to the at least one conduit.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings are primarily for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawing, like reference characters generally refer to like features (e.g., functionally similar and/or structurally similar elements).

Figure 1:
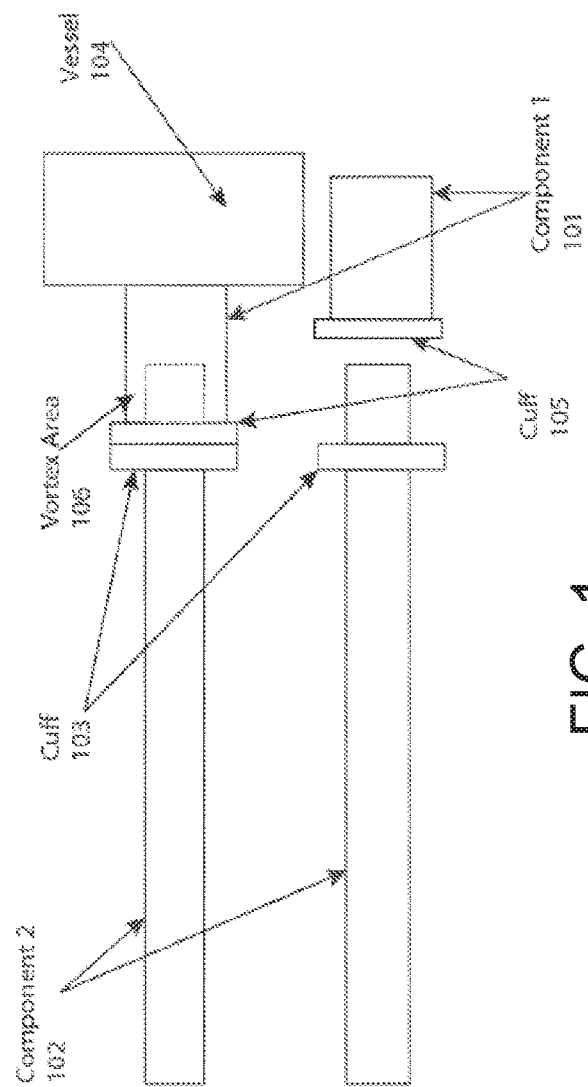
FIG. 1 shows a graft made of two components having different diameter and different characteristics in accordance with exemplary inventive embodiments.
Figure 2:
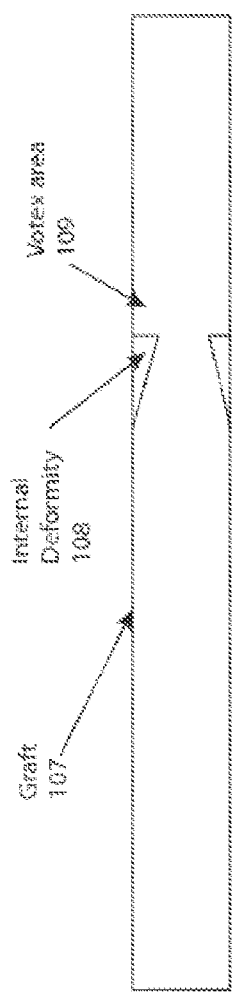
FIG. 2 shows a single graft having an internal structure to form a vortex that will limit any cellular buildup in that area in accordance with exemplary inventive embodiments.
Figure 3:
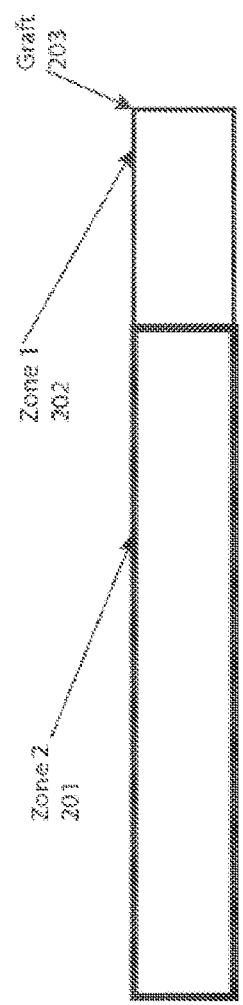
FIG. 3 shows a single graft with two areas including distinct internal structural characteristics that exhibit different reaction and behavior in the presence of blood flow in accordance with exemplary inventive embodiments.

The features and advantages of the inventive concepts disclosed herein will become more apparent from the detailed description set forth below when taken in conjunction with the drawings.

DETAILED DESCRIPTION

Following below are more detailed descriptions of various concepts related to, and exemplary embodiments of, inventive devices, systems, and methods for providing a graft anchor.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

The present disclosure provides, in certain aspects, a vascular graft 102 that comprises a first component 101 equipped with a suturing cuff 105 and a second component 102 equipped with another suturing cuff 103. First component 101 could be attached to a vessel 104 using commonly practiced suturing techniques or any other mechanical or non-mechanical anastomotic method. In some embodiments, first component 101 is made from a material that enhances cellular ingrowth in order to enhance graft biocompatibility. As such the material may by example be a porous EPTFE or a woven Dacron material.

The second component 102 may be smaller in diameter and equipped with a suturing cuff 103 to allow easy joining of first component 101 and second component 102 by means of commonly used sutures or any other mechanical or non-mechanical anastomotic methods.

The distal tip of the second component 102 typically protrudes inside the first component 101 and is somewhat concentric forming a gutter type circular annulus in between component 101 and component 102. Blood cells may deposit in this gutter and will as intended define the transition/boundary/seam between the cell ingrown to the smooth non cell ingrown area. In addition, second component 102 is made out of material that within the inner lumen inhibits cellular ingrowth or attachment, e.g. by a smooth and thin Silicone layer; therefore cellular ingrowth will be limited to first component 101. To further promote uninterrupted ingrowth defined by a smooth and thin layer of cells growing from the vessel into the first component 101, the first component 101 has been designed by its stiffness and potentially bellowed structure to serve as a shock absorbing agent for any blood pumping device, which may be attached to component 102. The shock absorbing agent manages to absorb any flow/pressure induced axial movement and as such helps to facilitate uninterrupted cell ingrowth in the preferred region. As such motion induced by the pumping device will not disturb the ingrowth, which may lead to continuous cell overgrowth, narrowing of the orifice and to irregular granular tissue, which also could dislodge and create ischemic events. While ingrowth into first component 101 is wanted, ingrowth onto the outside surface of first component 101 has to be avoided by cell inhibiting surface agents e.g. Silicone coating, since an overgrowth onto the outside of first component 101 could otherwise lead to target vessel deformation, which inherently may limit the orifice of the vessel near the anastomosis.

Due to the difference in lumen diameter between first component 101 and second component 102 a vortex is typically formed at vortex area 106 located in the proximity of the junction area of first component 101 and second component 102. Vortex area 106 serves as an area to limit the continual ingrowth or cellular attachment at vortex area 106.

In a different embodiment, the present disclosure provides, in certain aspects, a vascular graft 107 that is formed from a single or multiple tubular components that have similar inner diameter. Internal deformity 108 could be integral or added at a later stage of the graft manufacturing to form a "neck down" area in the inner lumen of graft 107. Inner deformity 108 serves as a bump to create a vortex in its proximity to inhibit cellular ingrowths, cellular attachment, and/or cellular deposit. The two sections of graft 107 separated by inner deformity 108 could be similar or different in biological characteristics, mechanical characteristics, and/or physical reaction to blood contact. While the area of graft 107 distal to internal deformity 108 may be surface treated to inhibit cellular ingrowth, the proximal area is designed to promote cellular ingrowth from the vessel onto the graft.

In a different embodiment, the present disclosure provides, in certain aspects, a vascular graft 203 that is formed by one or multiple zones, for example first zone 201 and a second zone 202, that make a single graft that possesses different biological characteristics, mechanical characteristics, and/or physical reaction to blood contact. In one embodiment zone 201 is infiltrated with Silicone rubber to inhibit cellular ingrowth, while zone 202 is of a porous/rough nature promoting ingrowth. The mating line between zone 201 and 202 is without a physical step, which avoids any unwanted overgrowth of cells from zone 202 onto zone 201.

Figure 4:
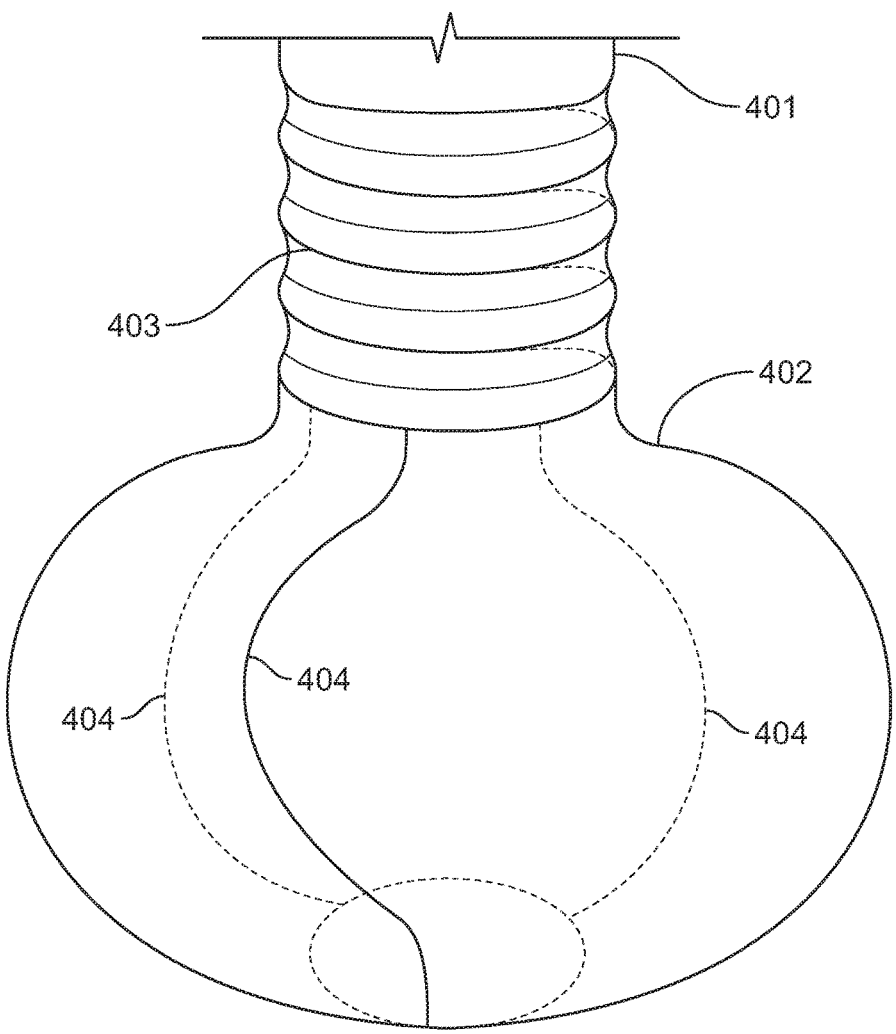
FIG. 4 illustrates a conduit having support structures in accordance with exemplary inventive embodiments.

FIG. 4 illustrates a support stent for a conduit, e.g., for use as a graft with a counterpulsation device (CPD). The conduit includes end ports and a passage there between that includes an enlarged area, e.g., bulb shaped portion. In some embodiments, e.g., when used with a CPD, blood may flow through the conduit in alternating direction. The conduit 401 includes a spiral support structure 403 on a first conduit region. Conduit 401 includes a bulbous portion 402 having a plurality of support structure 404 coupled thereto. Support structures 403 and 404 may be composed of stainless steel wire and may be coupled to the conduit via sutures in accordance with exemplary embodiments. The bulbous portion 402 may be flexible inwardly and outwardly to permit washing of the transition region. The bulbous portion 402 may be fabricated using a graft, such as a 20 mm graft, that is cut and sewn into the bulb shape illustrated in FIG. 4.

The conduit may be supported by a stent structure. In some embodiments, the support structure includes a first portion that includes one or more support struts shaped to form the bulb portion. In some embodiments, the outer surface of the material of the bulb portion of the conduit (e.g., PTFE or other suitable material), may be attached to the struts. In some embodiments, during use, this arrangement allows the bulb portion of the conduit to flex, e.g., to promote washing of the conduit passage In some embodiments, the support stent may include a second portion that supports a non-bulb shaped portion of the conduit (e.g., a portion with a substantially constant cross section). In some embodiments, the second portion may include a spiral shaped support structure. In some embodiments, the struts of the first portion of the support structure may be connected to the second portion of the support structure.

The support stent may be made of any suitable material (e.g., a biocompatible material with sufficient structural properties to support the conduit), including e.g., stainless steel or a shape memory material such as Nitinol.

In some embodiments, the conduit may be formed by one or multiple zones, for example first zone and a second zone, that make a single graft that possesses different biological characteristics, mechanical characteristics, and/or physical reaction to blood contact.

In one embodiment the first zone is infiltrated with Silicone rubber to inhibit cellular ingrowth, while the second zone is of a porous/rough nature promoting ingrowth. The mating line between zones may be without a physical step, which avoids any unwanted overgrowth of cells from the first zone to the second zone. Other embodiments may feature other transition shapes.

In some embodiments, the first zone may correspond to the bulb shaped portion while the second zone corresponds to the other portion, or vice versa.

Figure 5:
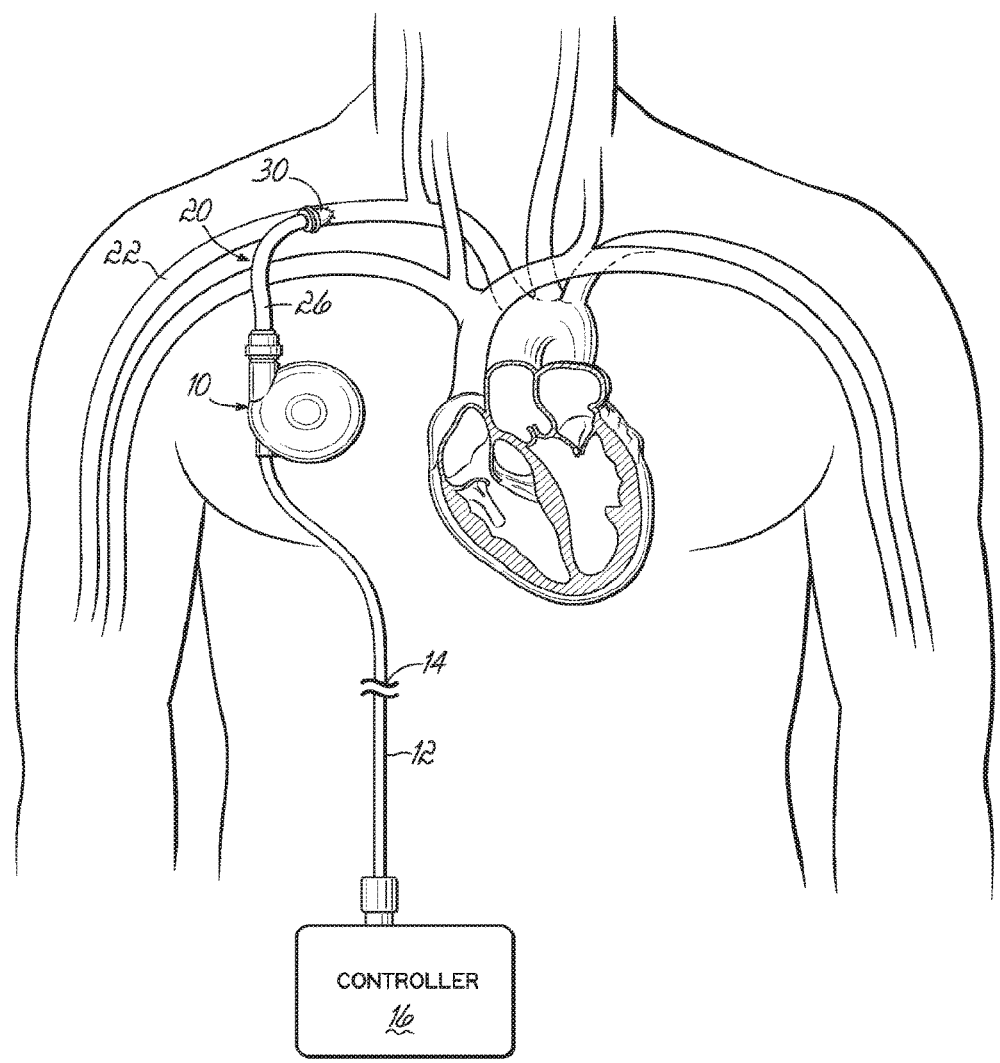
FIG. 5 shows a counterpulsation system in accordance with exemplary inventive embodiments.

One form of a counterpulsation system usable with inventive embodiments disclosed herein is shown in FIG. 5. Here a pump 10 is implanted in a pacemaker pocket on the patient's right side. Blood fills the pump 10 on one side and air or other fluid fills a sac or bladder (not shown) on the other side of the pump 10. An air drive line 12 is tunneled from the pacemaker pocket to a skin exit site 14, so the entire pump 10 is under the skin and can remain there chronically. After the driveline 12 exits the skin. It is attached to a small air drive unit 16 that controls shuttling of pressurized air in and out of the pump 10. A void in the pump 10 may be formed with the sac or bladder. The void fills with air as the heart beats (less cardiac work in ejecting blood) and empties to return blood into the circulation (more flow to the patient). The pump 10 is attached to the circulation with a conduit 20. The conduit 20 shuttles blood between the patient's circulatory system and the pump 10. This situation allows a patient to have chronic counterpulsation with full mobility. For a patient with severe and potentially non-reversible cardiac dysfunction, this is a great advantage as it is possible to live a relatively normal life, apart from the need to carry a small battery powered drive console 16.

As described, the blood is shuttled in and out of the pump 10 with a conduit 20, which is connected, to the circulation. There are a number of considerations related to implantation and use of this conduit 20. First, almost every conduit has blood flowing in one direction, but this conduit 20 has blood alternating flow direction two times for each heart beat as the pump 10 fills and empties with each cardiac cycle. This creates a number of important issues, which will be described. A second potential difficulty with a conduit in this situation is that it will typically be sewn to the subclavian artery 22 or axillary artery which is located beneath the clavicle and often quite deep, so it is technically difficult for a surgeon to suture the end of the conduit 20 to the artery 22.

The problem of a conduit with bidirectional flow relates to the responses of blood and tissues to the interfaces with synthetic materials and the response is dependent on the direction of flood flow. Many medical devices, such as blood pumps, are connected to the patient's circulation with artificial graft material such as polyester materials like Dacron® or expanded, porous Teflon® (ePTFE) that will promote tissue or cell ingrowth. The inside of blood pumps is generally smooth and composed of metals or plastics. When blood flows from a smooth metal or plastic blood pump into a synthetic graft (such as polyester), the interface where the pump meets the conduit (plastic or metal to synthetic graft) is a stable junction and there tends to be little problem when blood flows forward through this junction.

Unfortunately, experience has shown that when blood instead flows from a synthetic graft such as polyester into a smooth surfaced blood pump, a deposit of blood elements including platelets and fibrin tends to deposit at the junction of the two materials—principally on the synthetic graft and overhanging the Inflow to the pump. These deposits, especially platelets, tend to attract more blood elements and large and often fragile deposits occur at this junction. These deposits can break tree from the junction and enter the blood pump and be sent through the patient's circulation. These deposits can flow anywhere, but if they arrive in an artery to the brain, a stroke can result. For this reason, many successful blood pumps employ a smooth synthetic conduit (such as silicone or urethane) for blood inflow into the pump.

The problem with counterpulsation is that blood is flowing in an alternating bidirectional manner. One solution would be to use a smooth silicone or urethane conduit, which would create a stable junction between the pump and the conduit where the blood enters into the pump. This solves the problem at the Inflow to the pump. However, when a silicone material is anastomosed (sewn) to an artery, the junction develops a heavy deposit of blood material (fibrin and platelets). So merely replacing the inflow conduit with a silicone surface is not satisfactory, it is tempting to merely have a silicone conduit and add a fabric extension, but this merely moves the problem that occurs at the junction of the rough textured surface of the graft and the pump to the junction between the graft and the silicone tube or cannula.

Figure 8:
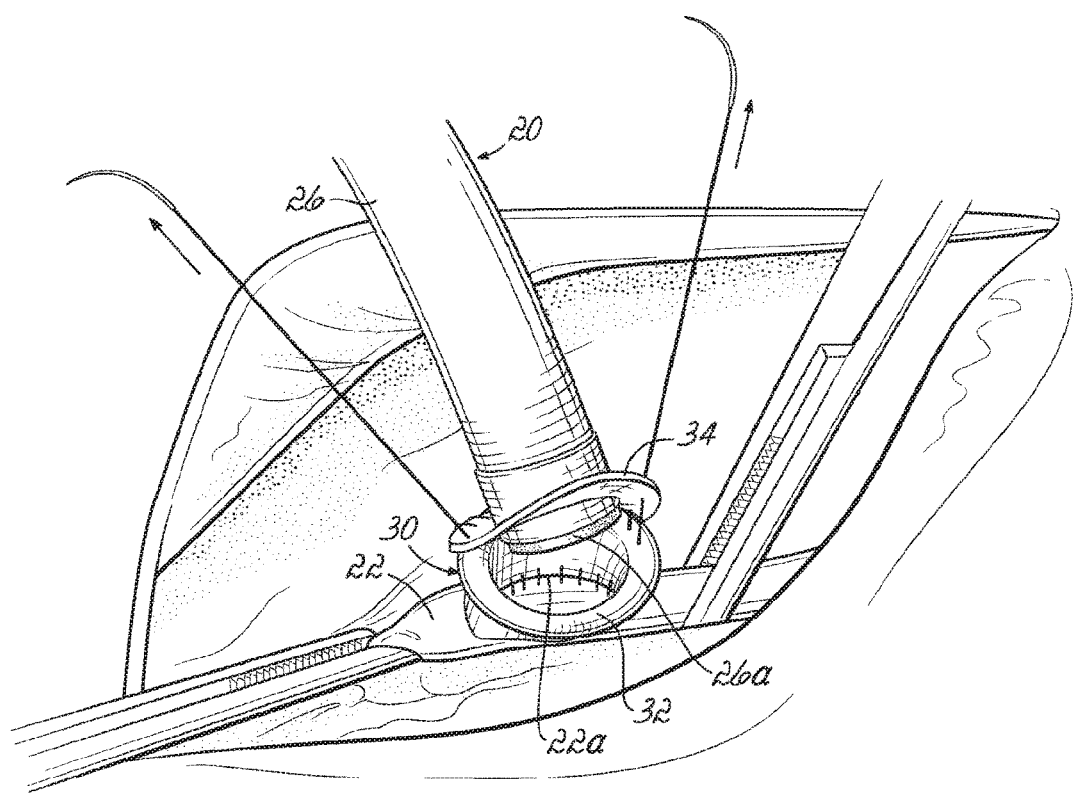
FIGS. 8 and 9 show how the two flanges of graft components are coupled in accordance with exemplary inventive embodiments.

FIG. 8 shows one exemplary solution in a cross-sectional view. The subclavian artery 22 is shown at the top of the figure. A "bubble" or enlarged area 24 of Dacron®. Teflon® or other material is sewn to the artery 22. A silicone or other smooth material conduit portion 26 is connected to the other side of the enlarged area 24. Rather than a direct junction, a special Interface is created. The smooth silicone surface portion 26 extends with a tip portion 26a several millimeters inside the enlarged area 24 of fabric or other material. The walls of the silicone tip portion 26a do not contact the fabric or material of the enlarged area or bubble 24, this avoids a silicone-to-fabric (or smooth-to-rough) point of contact.

Figure 12:
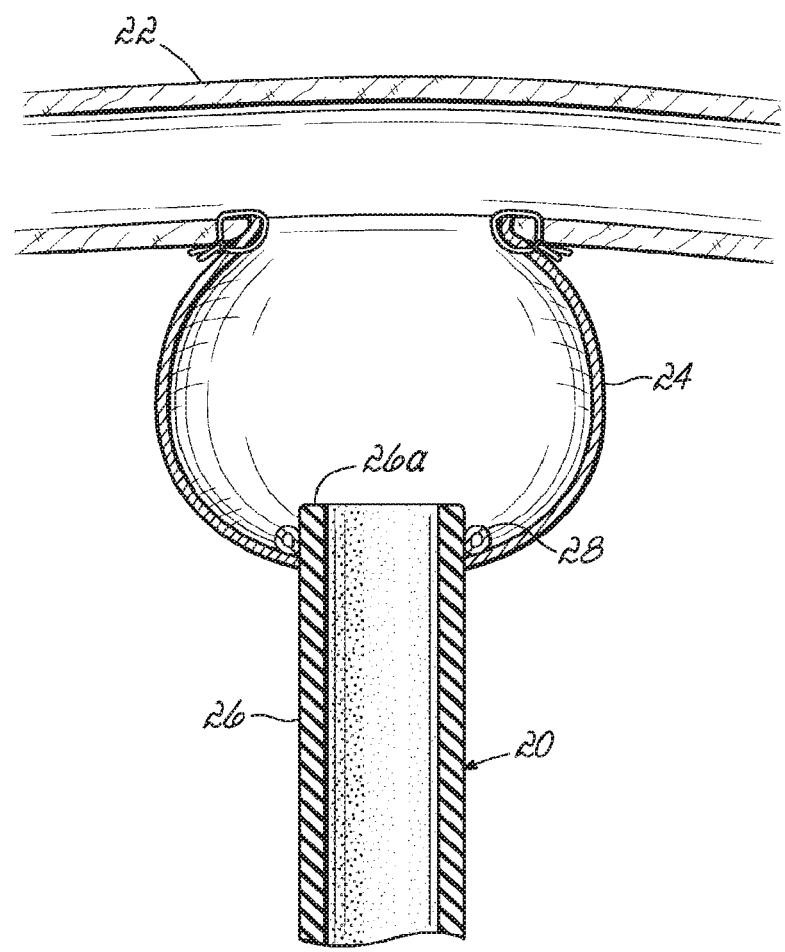
FIG. 12 shows a cross sectional view of a graft component in accordance with exemplary inventive embodiments.

Heart valves have been constructed with arrangements to avoid tissue ingrowth into the valve by creating an elevation—so that there is not a continuous connection between the fabric surface and the smooth surface. This elevation prevents tissue from growing over into junction point and creating a point where platelets and fibrin are deposited. The use of a small washer of material may also be of use. FIG. 12 shows a small washer 28 around the base of the tip 26a that may help arrest the attachment of blood elements.

Figure 13:
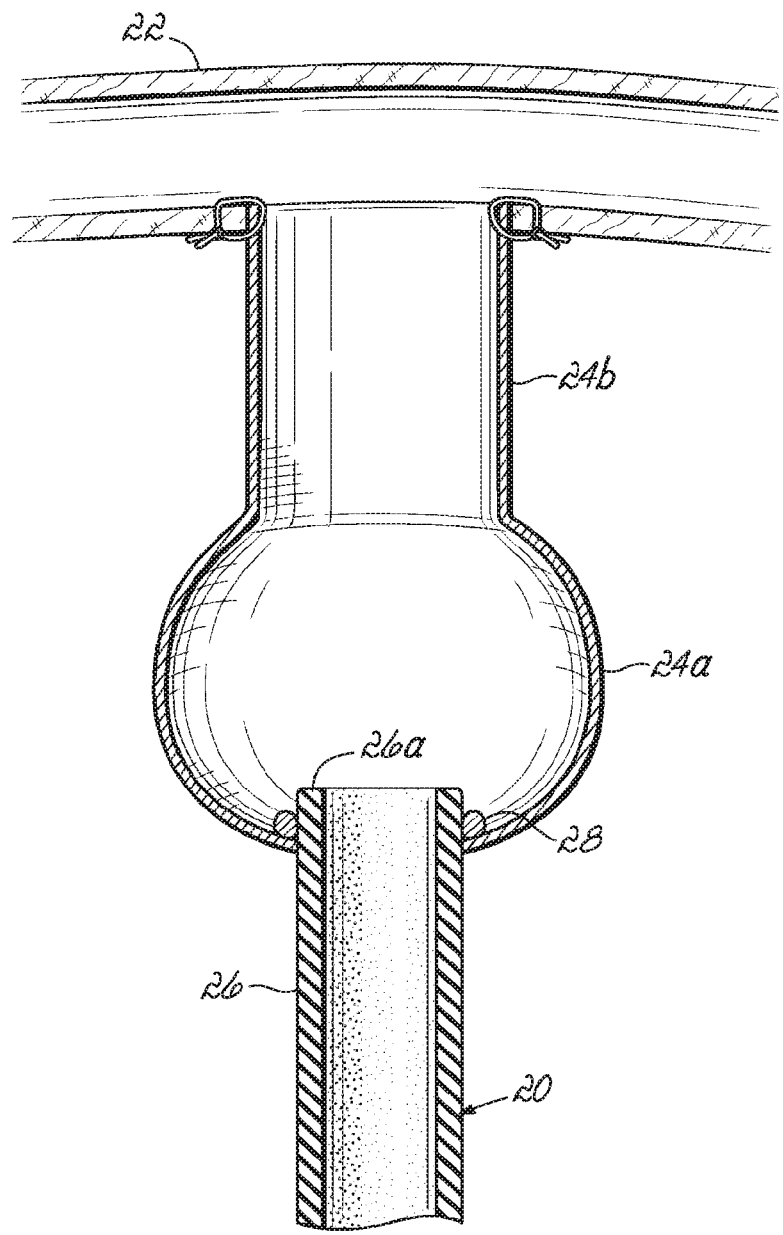
FIG. 13 shows an arrangement of the "bubble" or enlarged area of graft material located away from the anastomosis.

FIG. 13 shows that this arrangement of the "bubble" or enlarged area 24a of graft material is located away from the anastomosis. Specifically, enlarged area 24a is coupled to or includes an extension 24b that is anastomosed to the artery 22. Other features may be as described previously.

Figure 14A:
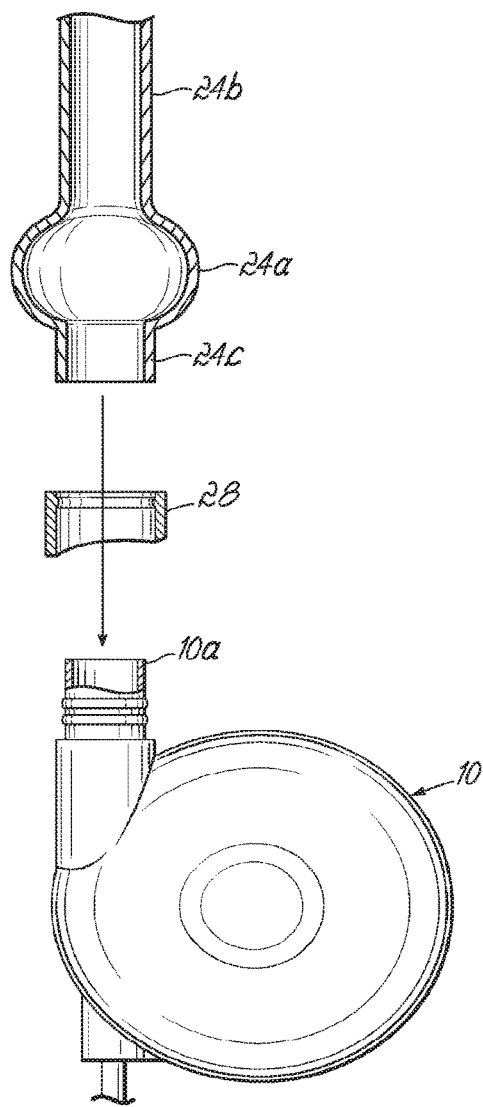
FIGS. 14A and 14B illustrate a pump connected to a graft component in accordance with exemplary inventive embodiments.
Figure 14B:
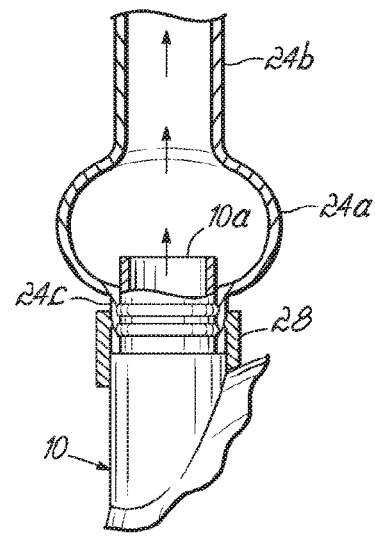

FIGS. 14A and 14B show a similar arrangement can be made at the junction of the pump 10, Here, the plastic, metal or other smooth surfaced junction or tip portion 10a of the pump 10 is separated from the rough surface of the enlarged graft material by a bubble interface 24a. An extension 24b of the graft material is sewn on the artery 22 (FIG. 13) as previously described. Another extension 24c on the opposite end may facilitate connection to the pump interface or tip portion 10a, along with a suitable connector 28. The junction or Interface 10a, which serves as an inlet/outlet port that extends into, but does normally not contact, the graft material 24a in use.

These devices with bubbles or enlargements could be made in one piece. As described previously, the subclavian artery 22 is located fairly deep and the incision is small. So a surgeon who is trying to sew a graft with a bubble or enlargement on it is working in a deep hole. The bubble or enlargement on the end of a graft obscures his view of the artery. It would be useful to avoid this problem and also satisfy the need for maintaining the arrangement where the smooth and rough surfaces are not in direct linear contact.

Figure 6:
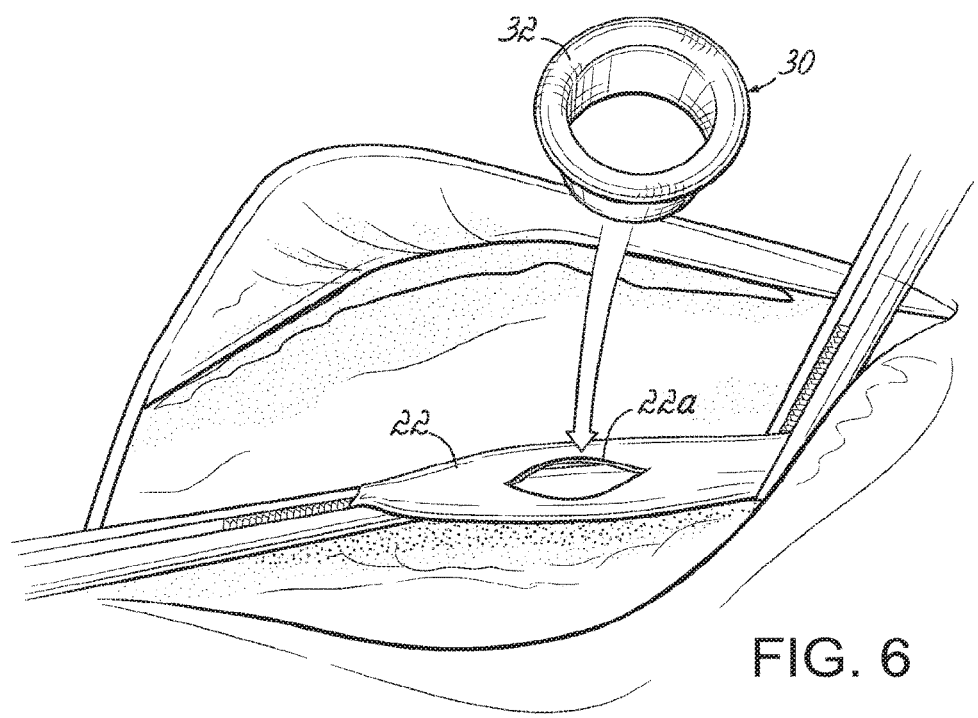
FIGS. 6 and 7 illustrate surgical implanting of a graft component in accordance with exemplary inventive embodiments.
Figure 7:
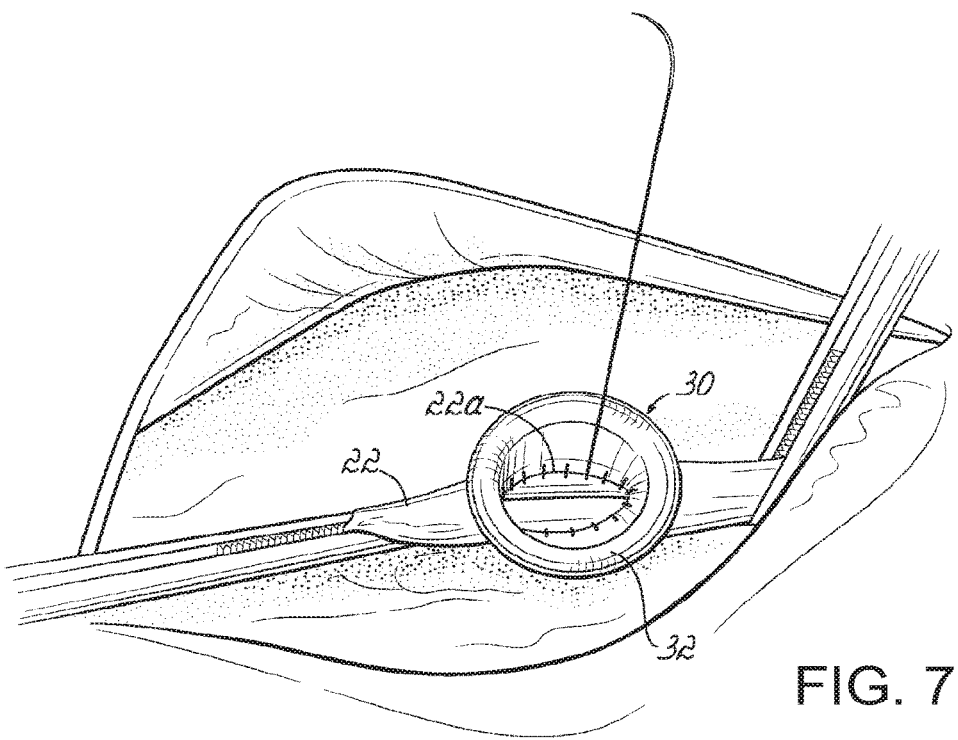

Such a solution is shown In FIGS. 6 and 7. Here, a graft element form from material such as described above is sewn to the artery. The graft element 30 has a flange 32 at one end. The element 30 is small and easy to move around, so does not obscure the view of the surgeon. FIG. 7 shows that it is easy to sew this element 30 around an opening 22a on the artery 22.

FIG. 8 shows how a junction between the silicone material portion 26 of the conduit 20 and the graft element 30 is recreated when a rim or flange 34 of sewing material or graft material, for example, of the conduit portion 26 is affixed to the flange 32 on the element 30 previously anastomosed to the artery 22.

Figure 9:
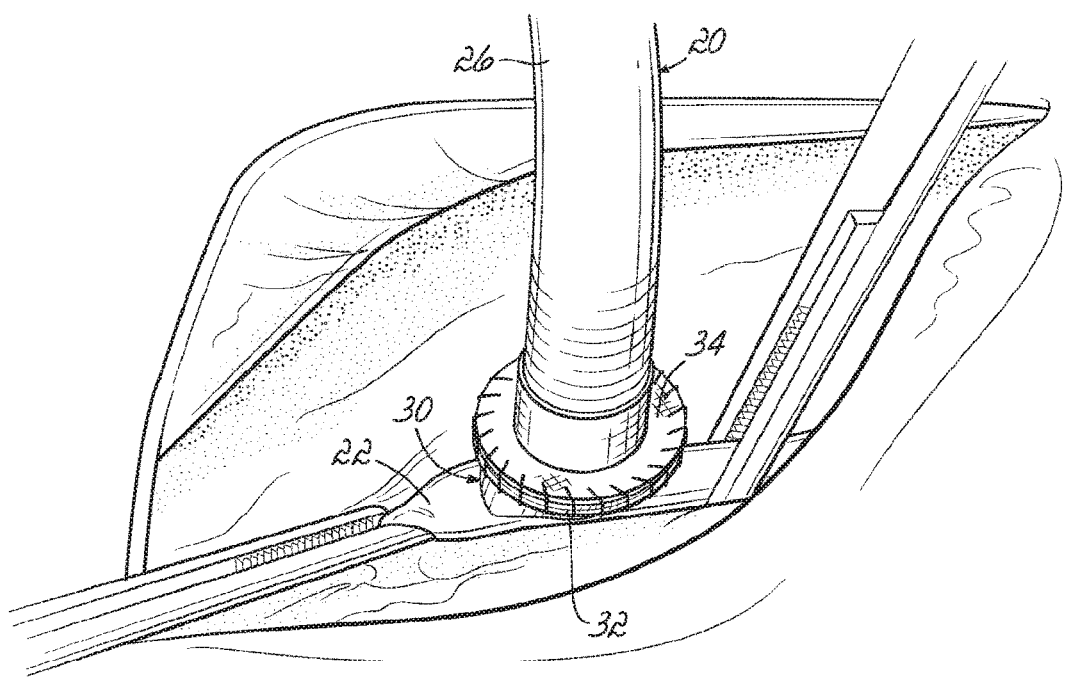

FIG. 9 shows how the two flanges 32, 34 are sewn together. This is a very easy anastomosis to perform.

It will be appreciated that these flanges 32, 34 could be joined not just by sutures but by staples, clips, glues, clamps etc.

Figure 10A:
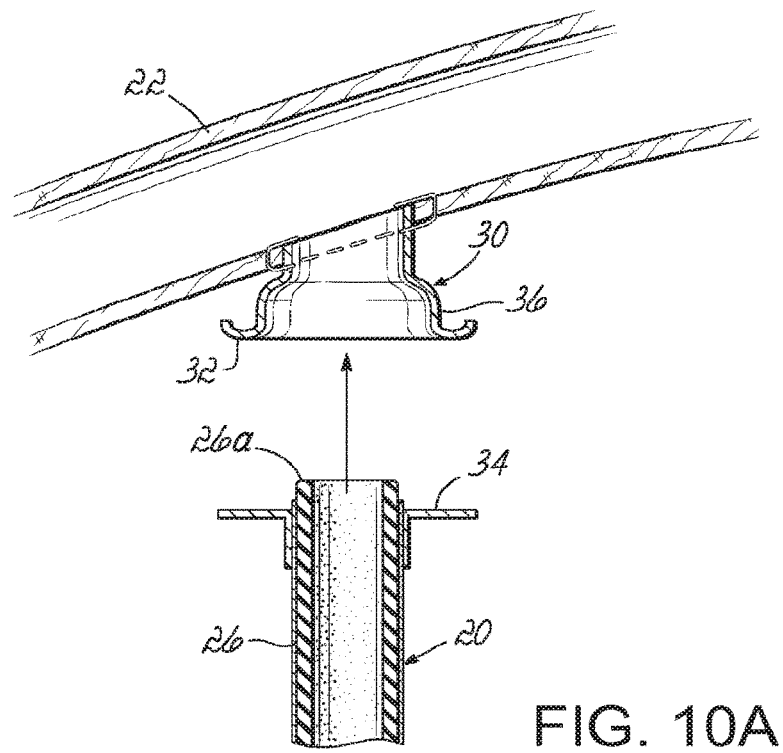
FIGS. 10A and 10B show side cross sectional views of the coupled graft components of FIGS. 8 and 9.

FIG. 10A shows a side cross sectional view of the two flanges 32, 34 coming together.

Figure 10B:
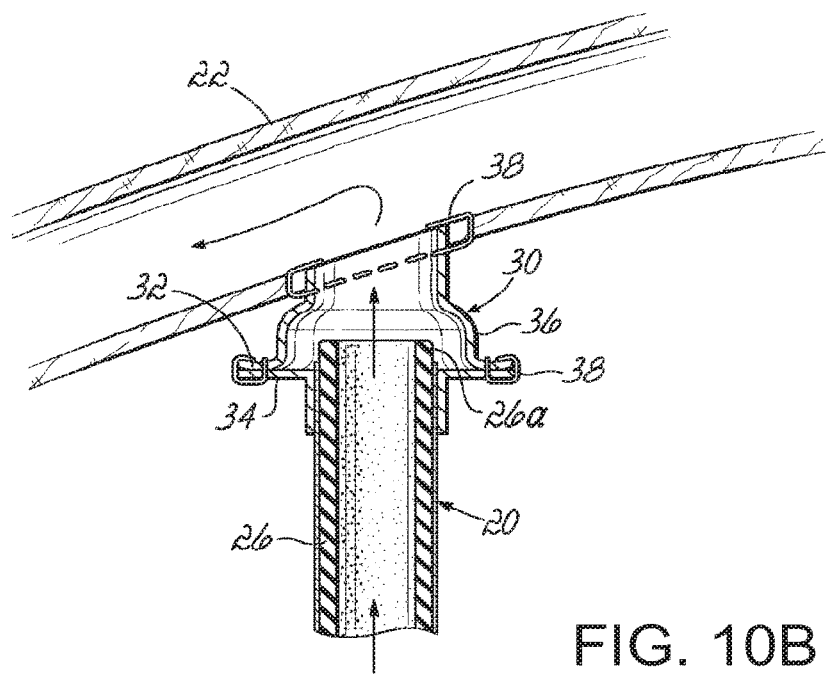

FIG. 10B shows how the bubble or enlarged connector 30 does not have to be flat—it could be beveled. Also the connector 30 does not have to be a generally spherical bubble as shown elsewhere herein. The key is only that the enlarged area keeps the silicone and graft surfaces (that Is, smooth and rough flow surfaces) from direct contact at their junction during use.

The bubble or enlarged area 36 is quite useful as it allows the graft to move or "swivel" Inside the bubble 36 and still not contact the wall of the bubble 36.

FIG. 10B also shows clips or staples 38 attaching the connector 30 to the artery 22 and attaching the flanges 32, 34 together.

The conduit portion 26 does not have to be entirely silicone. It could have any Inner core that presents a compatible surface to the exposed blood. For example, the inside could be metal, have a metal spiral reinforcement, etc. it could also have graft material inside like ePTFE or other polyester.

The smooth surface does not have to be silicone. This is used as representative of a smooth surface. The surface could be a metal or plastic (such as in the pump connection shown in FIGS. 14A and 14B.)

Figure 11:
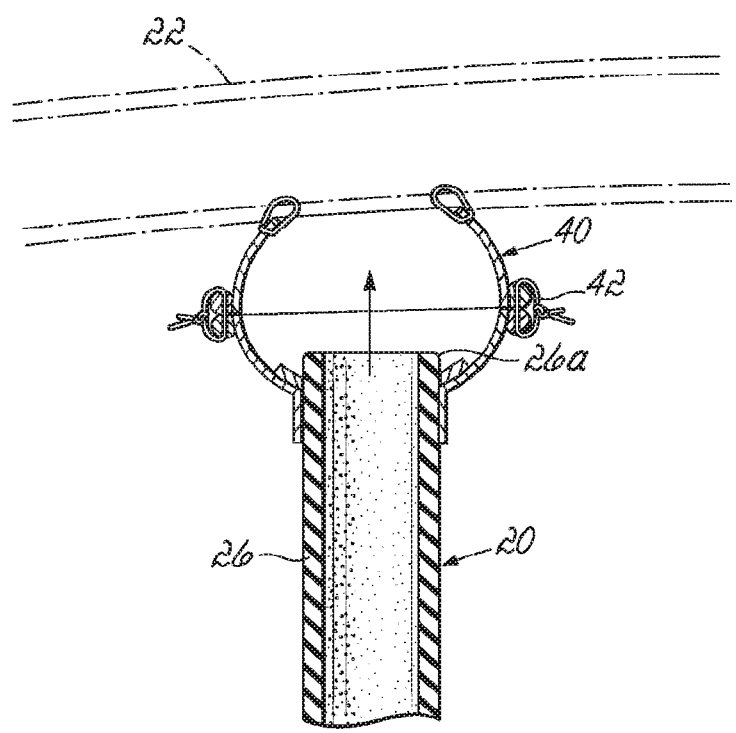
FIG. 11 shows a bubble or enlarged area constructed by "splitting" the bubble in the middle of the hemisphere.

FIG. 11 shows a bubble or enlarged area 40 constructed by "splitting" the bubble In the middle of the hemisphere. It could be equally possible in form the junction 42 anywhere In this arrangement; the location at the hemisphere is merely an example Alternatively, a more complete bubble could be created and the silicone cannula could be slipped into a defect at the end to perform the same function.

It should be noted that the terms used are basically smooth (silicone, plastics, metals) and rough or textured surfaces (Dacron, Teflon, ePTFE). It is also possible to have a tightly woven or knitted material that is typically called a textile, but could function as a smooth surface.

Also, It is possible to create a tightly woven polyester that behaves like a smooth surface. It could be possible to bring a tightly woven sewable graft into direct contact with a silicone surface without an intervening "bubble" or step.

It may also be important to prevent these conduits from collapsing as they can be located below the skin and could be crushed by a patient lying on them. Reinforcement of the conduits with plastic or wire spirals or rings can be used here. In addition, extra thicknesses of polymer or plastic could be added make them stronger.

In various embodiments, any of the devices and techniques described herein may be used in any suitable combination with the devices and techniques described in the Appendices.

As utilized herein, the terms "approximately," "about." "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of spring systems or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, describes techniques, or the like, this application controls.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

The invention claimed is:

1. A vascular graft comprising:
   at least one conduit having a first conduit region and a second conduit region, the first conduit region and the second conduit region being collinear and formed in a single tubular component with an inner lumen, wherein the first conduit region is connected to a first end of the second conduit region, and a second end of the second conduit region contains an opening for connection to a vessel; and
   at least one perturbation formed in the inner lumen and separating the first conduit region and the second conduit region, the perturbation configured to form a neck down area in the inner lumen to create a vortex in the second conduit region,
   wherein an area of the graft distal to the at least one perturbation is configured to inhibit cellular ingrowth, and an area of the graft proximal to the at least one perturbation is configured to promote cellular ingrowth.

2. The vascular graft according to claim 1, wherein the first conduit region includes a first material and the second conduit region includes a second material distinct from the first material.

3. The vascular graft according to claim 2, wherein the first material includes silicone rubber.

4. The vascular graft according to claim 2, wherein the second material includes porous ePTFE.

5. The vascular graft according to claim 2, wherein the second material includes a woven polyester material.

6. The vascular graft according to claim 1, wherein the at least one perturbation decreases the diameter of the conduit region.

7. The vascular graft according to claim 1, wherein the at least one perturbation is tapered.

8. The vascular graft according to claim 1, wherein the first conduit region and the second conduit region have substantially the same diameter.

9. The vascular graft according to claim 1, further comprising a blood flow assist system coupled to the at least one conduit.

* * * * *